United States Patent
Prasad

(10) Patent No.: US 11,819,538 B1
(45) Date of Patent: Nov. 21, 2023

(54) COLLAGEN DAILY WITH ENZYME INHIBITORS FOR ANTI-AGING

(71) Applicant: Kedar Prasad, San Rafael, CA (US)

(72) Inventor: Kedar Prasad, San Rafael, CA (US)

(*) Notice: Subject to any disclaimer, the term of this patent is extended or adjusted under 35 U.S.C. 154(b) by 0 days.

(21) Appl. No.: 17/835,689

(22) Filed: Jun. 8, 2022

(51) Int. Cl.
| | |
|---|---|
| A61K 38/39 | (2006.01) |
| A61K 31/728 | (2006.01) |
| A61K 31/19 | (2006.01) |
| A61K 31/047 | (2006.01) |
| A61K 36/185 | (2006.01) |
| A61K 36/82 | (2006.01) |
| A61K 45/06 | (2006.01) |
| A61K 38/00 | (2006.01) |
| A61Q 90/00 | (2009.01) |

(52) U.S. Cl.
CPC ............ *A61K 38/39* (2013.01); *A61K 31/047* (2013.01); *A61K 31/19* (2013.01); *A61K 31/728* (2013.01); *A61K 36/185* (2013.01); *A61K 36/82* (2013.01); *A61K 38/005* (2013.01); *A61K 45/06* (2013.01); *A61Q 90/00* (2013.01)

(58) Field of Classification Search
None
See application file for complete search history.

(56) References Cited

PUBLICATIONS

Collagen Peptides. Product page https://www.amazon.com/Resveratrol-Hyaluronic-Gooseberry-BioPerine-Anti-Aging/dp/B09ZPZ4QCG (Year: 2022).*

Majeed et al. "Standardized Emblica officinalis fruit extract inhibited the activities of alpha-amylase, alpha-glucosidase, and dipeptidyl peptidase-4 and displayed antioxidant potential" J. of the Science of Food and Agriculture. 100:509-516. (Year: 2020).*

Multi Collagen Protein Capsules. Product Page, Codeage Corporation, https://www.codeage.com/products/multi-collagen-protein-capsules (Year: 2020).*

Fujii et al. "Effects of amla extract and collagen peptide on UVB-induced photoaging in hairless mice" J. Functional Foods 5:451-459. (Year: 2013).*

Tomosugi et al. "Effect of Collagen Tripeptide on Atherosclerosis in Healthy Humans" J. Atherosclerosis and Thrombosis 24:530-538. (Year: 2017).*

* cited by examiner

Primary Examiner — Sudhakar Katakam
Assistant Examiner — Zachary J Miknis
(74) Attorney, Agent, or Firm — Dan De La Rosa

(57) ABSTRACT

ABSTRACT:
A formulation of Collagen peptides with enzyme inhibitors and hyaluronic acid would increase the levels of collagen and elastin and hyaluronic acid for a long period of time, and would decrease the rate of aging, and age-related changes in the skin and other organs. During aging, the levels of these molecules decrease because of enhanced activities of their respective enzymes. Current approach has utilized collagen peptides alone to increase the levels of collagen and elastin in order to maintain healthy skin. In the absence of inhibitors of enzymes collagenase and elastase, and hyaluronic acid, the levels of collagen peptides, elastin, and hyaluronic acid would decrease. Consequently, the beneficial effects of collagen peptides alone would be reduced within a short period of time.

8 Claims, No Drawings

COLLAGEN DAILY WITH ENZYME INHIBITORS FOR ANTI-AGING

FIELD OF THE INVENTION

The invention relates to a supplement for human consumption that is designed to improve the levels of collagen, elastin, and hyaluronic acid in humans.

BACKGROUND

After 30 years of age, a gradual decline in the levels of collagen, elastin, and hyaluronic acid occurs. This decline in the levels of collagen, elastin, and hyaluronic acid is due to their enhanced degradation by the enzymes collagenase, matrix metallopeptidases (MMPs), elastase, and hyaluronidase. Decreased levels of collagen causes thinning of the skin, reduced levels of elastin causes loss of elasticity of the skin, and reduction in the levels of hyaluronic acid causes dehydration of the skin. Because of above changes, the skin becomes thinner, looks sagging, drier, and wrinkled. In addition to skin aging, bones become weaker and fragile, cartilage in the joints becomes degenerated, decrease in muscle function reduces the mobility and balance. These studies suggest that maintaining sufficient levels of collagen, elastin, and hyaluronic acid may reduce rate of aging of the skin, age-related disfunction of other organs, and improve your health and appearance. However, there are no effective and prolonged ways to improve the levels of collagen, elastin, and hyaluronic acid in humans.

Use of commercial collagen peptides has improved the levels of collagen, elastin, and hydration somewhat, but these effects on the skin are reduced after a short period of time, because no efforts were made to inhibit the enzymes that break down these molecules in the skin. Such commercial collagen peptides alone is not sufficient to reduce rate of aging and age-related changes in the skin and other organs. In order to avoid the problems associated with the use of collagen peptides alone, this invention (called Collagen Daily) with enzyme inhibitors was invented.

These and other advantages will become apparent to those skilled in the relevant art upon a reading of the following descriptions.

The foregoing examples of the related art and limitations related therewith are intended to be illustrative and not exclusive. Other limitations of the relevant art will become apparent to those of skill in the art upon reading the specification and studying of the drawings.

SUMMARY OF THE INVENTION

As required, detailed embodiments of the present invention are disclosed herein; however, it is to be understood that the disclosed embodiments are merely exemplary of the invention that may be embodied in various forms. Therefore, specific structural and functional details disclosed herein are not to be interpreted as limiting, but merely as a basis for the claims and as a representative basis for teaching one skilled in the art to variously employ the present invention. The following implementations and aspects thereof are described and illustrated in conjunction with systems, tools, and methods that are meant to be exemplary and illustrative, not necessarily limiting in scope. In various implementations one or more of the above-described problems have been addressed, while other implementations are directed to other improvements.

In an embodiment, a formulation comprising at least one collagen peptide, and at least one enzyme inhibitor, and combinations and mixtures thereof.

In another embodiment, a formulation wherein at least one peptide are selected from a group comprising of bovine collagen peptides type I and bovine collagen peptides type III, and combinations and mixtures thereof.

In a further embodiment, a wherein at least one peptide is in an amount from about 1 g to about 100 g.

In yet another embodiment, a formulation wherein at least one enzyme inhibitor selected from a group comprising of enzyme inhibitor from Amla (Emblica officinalis) fruit extract, enzyme inhibitor from white tea decaffeinated extract and combinations and mixtures thereof.

In yet a further embodiment, a formulation wherein at least one enzyme inhibitor is in an amount from about 10 mg to about 1,000 mg.

In still another embodiment a formulation further comprising at least one humectant, said at least one humectant is chosen from a group comprising hyaluronic acid, glycerin, pyrrolidone carboxylic acid, and mixtures and combinations thereof.

In still a further embodiment a formulation of wherein at least one humectant is in an amount from about 10 mg to about 500 mg.

In another embodiment a formulation wherein the formulation should be taken at least once a day.

In a further embodiment a formulation wherein the formulation may be taken at least twice a day.

In still another embodiment a formulation wherein the formulation is designed to reduce the rate of aging of human organs.

In still a further embodiment a formulation wherein the formulation is designed to reduce the rate of collagen aging of human joints.

In yet another embodiment a formulation wherein the collagen peptides function to improve changes in the skin associated with aging.

In yet a further embodiment a formulation wherein the enzyme inhibitor functions prevent the degradation of newly formed collagen and elastin.

In another embodiment a formulation wherein the humectant functions to increase the moisture in aging skin.

In a further embodiment a composition comprising: Bovine collagen peptides in an amount from about 1 g to about 100 g; Amla fruit extract is in an amount from about 10 mg to about 1,000 mg; White tea decaffeinated extract is in an amount from about 10 mg to about 1,000 mg; Hyaluronic acid (as sodium hyaluronate) is an amount from about 10 mg to about 500 mg; and mixtures and combinations thereof.

In still another embodiment a method of manufacturing a formulation, the method comprises: admixing ingredients comprising at least one peptide and at least one enzyme inhibitor.

In still a further embodiment a method wherein at least one peptides are selected from a group comprising of bovine collagen peptides type I and bovine collagen peptides type III, and combinations and mixtures thereof.

In yet another embodiment a method wherein at least one at least one enzyme inhibitor chosen from a group comprising enzyme inhibitor from Amla (Emblica officinalis) fruit extract, enzyme inhibitor from white tea decaffeinated extract and combinations and mixtures thereof.

In yet a further embodiment a method further comprising: admixing at least one humectant to the mixture.

In another embodiment a method wherein at least one humectant is selected from a group comprising hyaluronic acid, glycerin, pyrrolidone carboxylic acid, and mixtures and combinations thereof.

DETAILED DESCRIPTION

The supplementation with collagen peptides alone is not sufficient to reduce the rate of aging and age-related changes in the skin and other organs for a prolonged period of time. This invention claimed to solve the problems associated with the use of collagen peptides alone.

During aging, the activities of enzymes collagenase, elastase, and hyaluronidase increase causing break down of collagen, elastin, and hyaluronic acid, respectively. This invention uses collagen peptides with inhibitors of enzymes and hyaluronic acid which would prevent the degradation of the levels of collagen, elastin, and hyaluronic acid in the skin. Therefore, Collagen Daily with enzyme inhibitors would lead to increased elasticity of the skin, reduced skin wrinkles and sagging, recovered lost cartilage tissue, decreased activity-related joint pain, strengthened tendons and ligaments, increased body mass in elderly men and premenopausal women, enhanced bone mineral density in post-menopausal women, and improved mobility and muscle function for a prolonged period of time.

This invention of Collagen Daily with enzyme inhibitors contains collagen peptides, inhibitor of enzymes from Amla fruit extract and white tea decaffeinated extract and hyaluronic acid. Supplementation with Collagen Daily would reduce the rate of aging and age-related changes in the skin and other organs.

Oral supplementation with this invention (Collagen Daily) would elevate the levels of collagen and elastin, and while supplementation with hyaluronic acid would increase the levels of hyaluronic acid. If enzyme inhibitors are not used, these molecules would be degraded by their respective enzyme. Consequently, the beneficial effects of collagen peptides on aging would be markedly reduced. Therefore, it is essential to add inhibitors of enzymes in order to maintain their elevated levels for a long period of time. Two sources of enzyme inhibitors from Amla fruits extracts and white tea decaffeinated extracts were used because combination of different enzyme inhibitors from these sources are more effective in preventing the degradation of collagen and elastin than that produce by one source. In another embodiment, sapodilla fruit extract could be used in preventing the degradation of collagen and elastin than that produce by one source.

The activities of enzymes collagenase, elastase, and hyaluronidase, which degrade collagen, elastin, and hyaluronic acid, increase during aging of the skin and other organs. This invention of Collagen Daily with enzyme inhibitors would prevent rise in the activities of these enzymes, and thereby, may reduce the rate of aging and age-related changes in the skin and other organs. This invention of Collagen Daily with enzyme inhibitors may produce following health benefits: (a) increases the levels of collagen, hydration, and elasticity of the skin, (b) reduces skin sagging and wrinkles, (c) recovers lost cartilage tissue, (d) strengthen tendon and ligament, (e) decreases joint pain, (f) improves bone mineral density in post-menopausal women, (g) improves memory by removing beta-amyloids, which kill cholinergic neurons responsible for storing memory, from the brain, (h) improves memory and learning ability by increasing the levels of BDNF (brain-derived neurotrophic factor), (i) improves symptoms of sarcopenia (loss of muscle as we grow older), (j) reduces osteoarthritis pain, (k) reduces symptoms of Rheumatoid arthritis, and (l) helps in wound healing.

In order to properly manufacture or create this invention, an individual must have the following qualifications: (a) Individual must have extensive knowledge of biochemical changes that are involved in aging; (b) Individual must have done research on recent advances in collagen function; (c) Individual must know about enzyme collagenase which inhibits collagen, elastase which inhibits elastin, and hyaluronidase which reduces hyaluronic acid. Elevated levels of collagen, elastin, and hyaluronic acid would reduce the rate of aging of the skin and other organs; (d) Individual must have done research on the sources of enzyme inhibitors and their role in aging; and (e) Individual must have a full knowledge of commercial collagen peptides that are being marketed, and have the ability to critically analyze the benefits and limitations of such products.

This invention (Collagen Daily) with enzyme inhibitors are prepared in a powder form. Take orally using a scoop that contains 11.6 g of product once-a-day for the remaining of the lifespan. The mixture of collagen peptides can be taken with water or any liquid.

These and other examples provided in this paper are intended to illustrate but not necessarily to limit the described implementation. As used herein, the term "implementation" means an implementation that serves to illustrate by way of example but not limitation. The techniques described in the preceding text and figures can be mixed and matched as circumstances demand to produce alternative implementations.

Numerous modifications and variations of the present invention are possible in light of the above teachings. It is therefore to be understood that within the scope of the attendant claims attached hereto, this invention may be practiced otherwise than as specifically disclosed herein.

What is claimed is:

1. A formulation consisting of at least one collagen peptide, and at least one enzyme inhibitor, and at least one humectant, said at least one peptide are selected from a group consisting of bovine collagen peptides type I and bovine collagen peptides type III, and combinations and mixtures thereof, said at least one enzyme inhibitor selected from a group consisting of enzyme inhibitor from Amla fruit extract, enzyme inhibitor from white tea decaffeinated extract and combinations and mixtures thereof, and said at least one humectant is chosen from a group comprising hyaluronic acid, glycerin, pyrrolidone carboxylic acid, and mixtures and combinations thereof.

2. The formulation of claim 1 wherein said at least one peptide is in an amount from about 1 g to about 100 g.

3. The formulation of claim 1 wherein said at least one enzyme inhibitor is in an amount from about 10 mg to about 1,000 mg.

4. The formulation of claim 1 wherein said at least one humectant is in an amount from about 10 mg to about 500 mg.

5. The formulation of claim 1 wherein said formulation should be taken at least once a day.

6. The formulation of claim 1 wherein said formulation may be taken at least twice a day.

7. A composition consisting of:
Bovine collagen peptides in an amount from about 1 g to about 100 g;
Amla fruit extract is in an amount from about 10 mg to about 1,000 mg;

White tea decaffeinated extract is in an amount from about 10 mg to about 1,000 mg;

Hyaluronic acid is an amount from about 10 mg to about 500 mg; and mixtures and combinations thereof.

8. A method of manufacturing a formulation, said method comprises: admixing ingredients of claim 1.

\* \* \* \* \*